United States Patent [19]
Bobbitt et al.

[11] Patent Number: 5,614,073
[45] Date of Patent: Mar. 25, 1997

[54] METHOD AND APPARATUS FOR DETECTION OF UNDERIVATIZED AMINES AND AMINO ACIDS UTILIZING END COLUMN ADDITION OF $RU(BPY)_3^{2+}$

[75] Inventors: Donald R. Bobbitt, Fayetteville; Warren A. Jackson, Batesville, both of Ark.

[73] Assignee: Board of Trustees of the University of Arkansas

[21] Appl. No.: 403,464

[22] Filed: Mar. 13, 1995

[51] Int. Cl.$^6$ .................................................. G01N 27/26
[52] U.S. Cl. ..................... 204/452; 204/461; 204/603; 204/612
[58] Field of Search ........................ 204/229 R, 180.1, 204/452, 461, 603, 612

[56] References Cited

U.S. PATENT DOCUMENTS

| | | | |
|---|---|---|---|
| 5,147,806 | 9/1992 | Kamin et al. | 436/149 |
| 5,221,605 | 6/1993 | Bard et al. | 435/4 |
| 5,240,576 | 8/1993 | Lauer et al. | 204/180.1 |
| 5,298,427 | 3/1994 | Bobbitt et al. | 436/89 |

FOREIGN PATENT DOCUMENTS

| | | | |
|---|---|---|---|
| 0497488 | 1/1992 | European Pat. Off. | 204/299 R |

OTHER PUBLICATIONS

"Chemiluminescent detection of amino acids using in situ generated $Ru(bpy)_3^{3+}$", Warren A. Jackson and Donald R. Bobbitt, *Analytica Chimica Acta*, 285 (Jan. 1994) pp. 309–320, Elsevier Science B.V., Amsterdam (1994).

"Voltammetric and Chemiluminescent Characterization of a Heptyl–thiol Derivative of Ruthenium Tris Bipyridine Self-Adsorbed onto Indium Tin Oxide Substrates", Warren A. Jackson and Donald R. Bobbitt, *Michrochemical Journal* 49, pp. 99–109 (1994).

"Chemiluminescence Detection in Capillary Electrophoresis", Rajeev Dadoo, Luis A. Colón and Richard N. Zare, *Short Communications*, (Dec. 23, 1991).

"Chemiluminescence Detection Using Regnerable Tris (2,2'-bipyridyl)ruthenium(II) Immobilized in Nafion", Threse Malcom Downey and Timothy A. Nieman, *Anal. Chem.*, 1991, 64, pp. 261–268.

"Electrogenerated Chemiluminescent Determination of Oxalate", Israel Rubinstein, Charles R. Martin and Allen J. Bard, *Anal. Chem.*, 1983, 55, pp. 1580–1582.

"Electrogenerated Chemiluminescence. 37. Aqueous Ecl Systems Based on $Ru(2,2'-bipyridine)_3^{2+}$ and Oxalate or Organic Acids", Israel Rubinstein and Allen J. Bard, *J. Am. Chem. Soc.*, 1981, 103, pp. 512–516.

*Primary Examiner*—Bruce F. Bell
*Assistant Examiner*—Alexander Noguerola
*Attorney, Agent, or Firm*—Gilbreth & Strozier; J. M. Gilbreth

[57] ABSTRACT

Disclosed is a method for and an apparatus for detecing amines or amino acids, which apparatus generally includes a capillary electrophoresis separation tube with a post-capillary reactor positioned at the end of the tube to immediately receive separated samples from the tube. The post-capillary reactor includes a solution of $Ru(bpy)_3^{2+}$ buffered with a base. The post capillary reactor further includes an electrode assembly for providing current to the solution to convert nonluminescing $Ru(bpy)_3^{2+}$ to luminescing $Ru(bpy)_3^{3+}$. The method generally includes separating the desired analyte from the sample, contacting the analyte with the solution to produce luminescence, and then photometrically measuring the amount of analyte present as a function of the luminescence.

8 Claims, 7 Drawing Sheets

METHOD AND APPARATUS FOR DETECTION OF UNDERIVATIZED AMINES AND AMINO ACIDS UTILIZING END COLUMN ADDITION OF RU(BPY)$_3^{2+}$

BACKGROUND OF THE INVENTION

1. Field of the Invention

The present invention relates to a method of and apparatus for detecting chemicals. In another aspect, the present invention relates to a method of and apparatus for detecting amino acids and amines. In even another aspect, the present invention relates to a method of and apparatus for detecting amino acids and amines utilizing chemiluminescence in combination with capillary electrophoresis. In still another aspect, the present invention relates to a method of and apparatus for detecting amino acids and amines utilizing in situ generated chemiluminescence in combination with capillary electrophoresis having end column addition of a compound convertible into a chemiluminescence compound. In yet another aspect, the present invention relates to a method of and apparatus for detecting amino acids and amines utilizing in situ generated Ru(bpy)$_3^{3+}$ in combination with capillary electrophoresis having end column addition of Ru(bpy)$_3^{2+}$.

2. Description of the Related Art

Recent developments in the fields of molecular biology, genetic engineering and DNA sequencing have suggested that further advances will require improvements in the ability to sequence the amino acid composition of proteins by at least one to two orders of magnitude.

Currently available techniques for amino acid analysis usually involve pre- or post-column derivatization to enhance detection, since most amino acids have no inherent fluorophore or chromophore. These derivatization methods may involve reaction of the amino acid with either ninhydrin, phenylisothiocyanate, dansyl chloride, o-phthalaldehyde, 9-fluorenylmethyl chloroformater or other derivatizing agents in order to faciliate detection using conventional UV-visible or fluorescence spectroscopy. Other methods involve attachment of a chemiluminescent probe to the amino acid. In general, preparation of amino acid derivatives can be problematic as the procedures are often labor intensive, some derivatives may not be stable, and the moiety added to enhance detection may dominate the physio-chemical properties of the complex. This can complicate the separation of the various amino acid derivatives.

Not surprisingly, there have been suggestions in the prior art of techniques for the detection of underivatized amino acids.

Chemiluminescence has been suggested as a method for the detection of underivatized amino acids, following high performance liquid chromatography, either by providing Ru(bpy)$_3^{30+}$, see, U.S. Pat. No. 5,298,427, or by in situ generation of Ru(bpy)$_3^{3+}$, see, Downey and Nieman., Anal. Chem. 1992, 64, 261–268.

Electrophoresis in small diameter open Teflon tubes was introduced in 1979, see Mikkers et al., J. Chrom., 1979, 169, 11. Capillary electrophoresis separation was then demonstrated in 75 μm i.d. pyrex capillaries in 1981, see, Jorgenson et al., Anal. Chem., 1981, 53, 1298. Briefly, capillary electrophoresis is a separation technique which can provide extremely high efficiency separations based on electrophoretic mobility. The separation is electrical field driven and occurs in a 75 μm i.d. silica capillary. The high efficiency of the separation system provides a separated sample which is dispersed in approximately 10–50 nanoliters of buffer. Detection modes which are compatible with these requirements of small volume and dilute conditions are rare.

Capillary electrophoresis is generally performed with detection by UV absorption, in which typically, analyte concentrations of approximately $10^{-4}$ to $10^{-5}$M may be detected.

Chemiluminescence has also been suggested for use in combination with capillary electrophoresis. Dadoo et al. in "Chemiluminescence Detection in Capillary Electrophoresis", 1991, with the authors stating that "adaption of chemiluminescence to capillary electrophoresis appears promising because it is easily implemented."

However, detection of separated analytes following electrophoretic separation is much more challenging than detection following high performance liquid chromotography. The characteristics which make electrophoretic attractive separation technique also make detection difficult. The most obvious is the very small dimensions of the capillary itself and the minuscule volumes of analyte injected. Construction of off-column detection cells analogous to detection cells used for UV-vis, fluorscence, and electrochemical detection in high performance liquid chromatography is almost impossible due to the very small dead-volumes required for efficient detection without excessive zone broadening. Most absorbance, fluorescence, and other optical techniques employ on-column detection. This involves removal of some of the polyimide coating of the capillary at a position somewhere along the separation capillary. This spot is then the "detection cell". The detection capability of such a configuration is particularly hampered by this short pathlength.

In addition, the present inventors encountered other difficulties when adapting chemiluminescence to capillary electrophoresis utilizing a Ru(bpy)$_3^{3+}$ system.

Thus, the present inventors submit that the adaption of chemiluminescence to capillary electrophoresis, especially when utilizing a Ru(bpy)$_3^{3+}$ system is not an easy implementation.

There is a need in the art for an improved detection method and apparatus.

There is another need in the art for a detection method and apparatus for detecting amines and/or amino acids.

There is still another need in the art for a detection method and apparatus for detecting amines and/or amino acids which utilizes chemiluminescence and capillary electrophoresis.

This is yet another need in the art for a detection method and apparatus for detecting amines and/or amino acids which utilizes chemiluminescence and capillary electrophoresis in a Ru(bpy)$_3^{3+}$ system.

These and other needs in the art will become apparent to one of skill in the art upon review of this application.

SUMMARY OF THE INVENTION

It is an object of the present invention to provide for an improved detection method and apparatus.

It is another object of the present invention to provide for a detection method and apparatus for detecting amines and/or amino acids.

It is still another object of the prsent invention to provide for a detection method and apparatus for detecting amines and/or amino acids which utilizes chemiluminescence and capillary electrophoresis.

It is yet another object of the present invention to provide for a detection method and apparatus for detecting amines and/or amino acids which utilizes chemiluminescence and capillary electrophoresis in a $Ru(bpy)_3^{3+}$ system.

These and other objects of the present invention will become apparent to one of skill in the art upon review of this application.

According to one embodiment of the present invention, there is provided an apparatus for detecting the presence apparatus an analyte in a sample. The apparatus of generally includes a capillary electrophoresis separation tube with a post-capillary reaction zone positioned for contacting separated analytes with a buffered solution. The reaction zone includes a buffered solution of $Ru(bpy)_3^{2+}$. Immediate the reaction zone is an electrode assembly for providing current to the buffered solution to convert nonluminescing $Ru(bpy)_3^{2+}$ to luminescing $Ru(bpy)_3^{3+}$. A photometric device is positioned to receive any luminescence from the reaction zone.

According to another embodiment of the present invention, there is provided a method of dectecting analytes in a sample. The method generally includes separating the analyte from the sample by electrophoresis and then contacting the separated analyte with a buffered solution of $Ru(bpy)_3^{2+}$. Next, the nonluminescing $Ru(bpy)_3^{2+}$ is electrically converted to luminescing $Ru(bpy)_3^{3+}$ to produce luminescence upon contact with the analyte. The next step is to photometrically measure the quantity of the analyte present as a function of the luminescence.

DETAILED DESCRIPTION OF THE INVENTION

Figure 2:
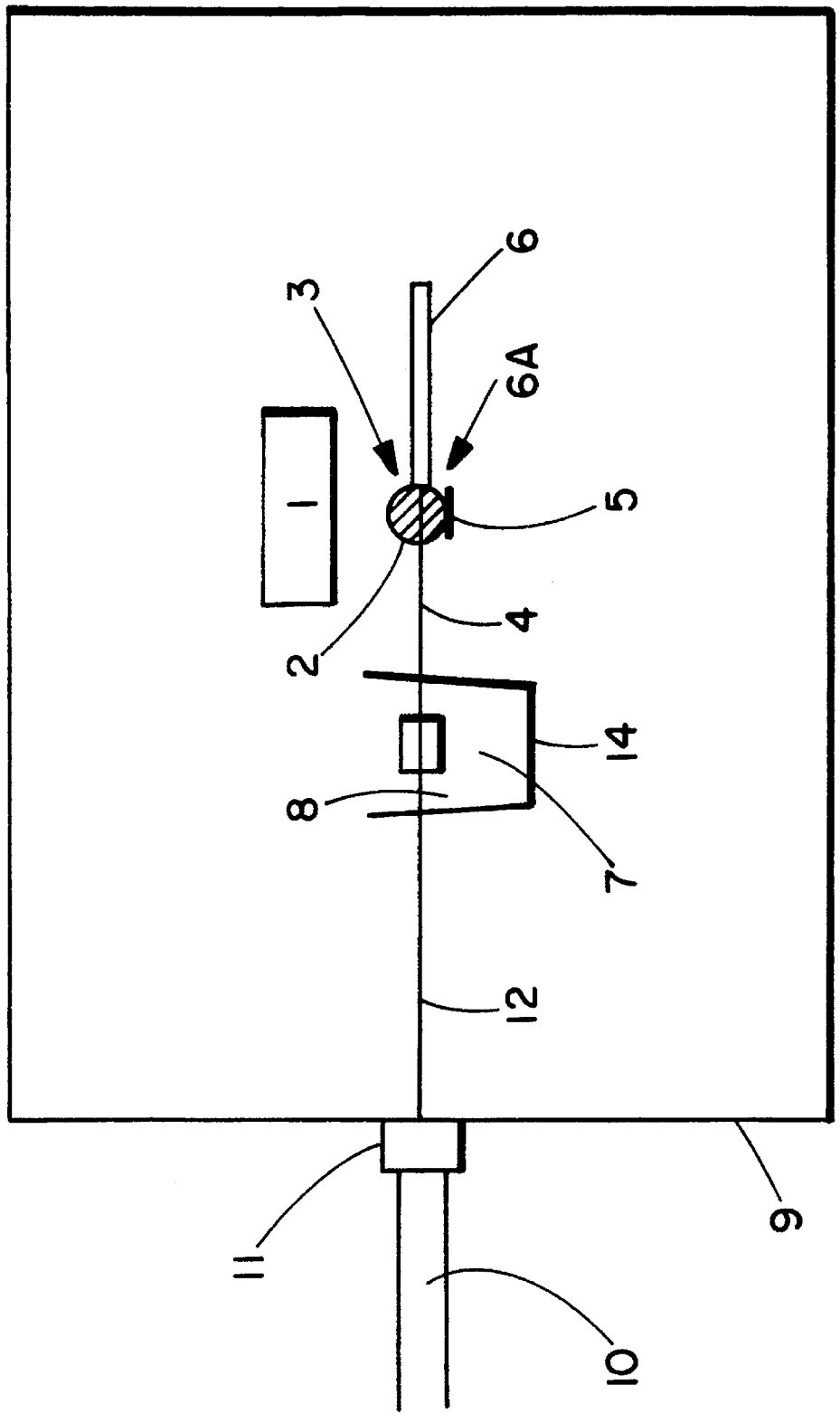
FIG. 2 is a schematic diagram of one embodiment of the apparatus of the present invention showing specifically photomultiplier tube 1, drop of electrolyte 2, SCE reference electrode 3, detection capillary 4, stainless steel spatula auxiliary electrode 5, carbon microfiber electrode assembly 6, support beaker 14 and Nafion joint 7, platinum cathode 8, dark box 9, PVC pipe 10 and rubber stopper 11.

The apparatus and method of the present invention are more easily understood by reference to FIG. 2 which is a schematic representation of one embodiment of the present invention.

As shown in FIG. 2, electrophoresis capillary 12 extends from protective sleeve 10. Protective sleeve 10 is nonconductive and nontransparent, and serves to both protect against operator injury and prevent against leakage of light into dark box 9. Plug 11, a rubber stopper in the embodiment shown, serves to further reduce the amount of light passing to dark box 9. Capillary 12 is electrically decoupled from detection capillary 4 to prevent electrical charge from passing to the detection capillary. Nafion sleeve joint 7 provides a liquid bridge between the capillaries to permit sample flow between capillary 12 and capillary 4. In the embodiment shown, beaker 7 serves to support each end of the Nafion joint. Platinum cathode 8 provides a ground for the electrophoresis capillary 12.

As shown in the embodiment of FIG. 2, capillary 4 passes the separated analyte into contact with buffer 2 in reaction zone Z.

In the embodiment shown, buffer 2 is a droplet positioned in the reaction zone Z. However, it is to be understood that buffer 2 can be provided to reaction zone Z in a stream form. In such a case, a stream of buffer 2 and a stream of analyte from capillary 4 are brought together at reaction zone Z to form one stream. Suitable methods include using a "T" or "Y" geometry to join the streams. Of course, any other suitable geometries may be utilized. With a "T", the steams contact each other at a 180° angle in a head-on collision and then exit through the leg of the "T". Alternatively, the streams could contact each other at 90°. In a "Y" configuration, the streams enter through the arms of the "Y" and exit through the base, with the angle of contact controlled by the angle of the arms. Using streams, zone of contact for the analyte and buffer 2 is considered the reaction zone.

Buffer droplet 2 includes nonluminescening $Ru(bpy)_3^{2+}$ which is converted to luminescening $Ru(bpy)_3^{3+}$ by electrical action of electrodes 3, 5 and 6. . As $Ru(bpy)_3^{3+}$ is unstable, one advantage of the present invention is the conversion to luminescening $Ru(bpy)_3^{3+}$ immediate the electrophoresis capillary, rather then from a remote site.

Reference electrode 3, carbon microfiber electrode assembly 6 and stainless steel spatula auxalary electrode 5 form an electrode assembly located immediate to the reaction zone. The carbon microfiber 6A of electrode assembly 6 is positioned as close to detection capillary 4 as possible without contact. In some instances, carbon microfiber 6A can even be positioned within capillary 4.

Photometric meter 1 is located immediate to the reaction zone in a position suitable to detect any luminescence from the reaction zone.

Where the reaction zone is located within a tube, capillary or other container, it is necessary to provide a "window" or light opening to permit luminescence to be detected by meter 1. Typically, meter 1 is a photomultiplier tube. The analog output of the photomultiplier tube is digitized and processed via a computer. Of course, suitable techniques to focus and/or direct the luminescence toward meter 1 may be utilized. Such techniques include the use of lens, mirrors or optical fibers.

In general, capillary electrophoresis separation techniques are well known in the art. It is to be understood that in the practice of the present invention, any suitable capillary electrophoresis separation technique may be utilized. Suitable electrophoresis techniques include those disclosed by Jorgenson et al., Anal. Chem., 1981, 53, 1298. and by Dadoo et al., in Anal. Chem., 1994, 66, 303, both herein incorporated by reference.

In the practice of the present invention, any suitable power supply may be utilized. In most instances, the power supply will need to provide on the order of 10 to about 50 kV of power. While higher voltages may provide faster separation, factors to consider while selecting the voltage utilized include ohmic heating and thermal gradients, both of which may negatively effect the separation.

The capillaries utilized in the electrophoresis system of the present invention may be selected from any suitable capillary. Glass capillaries suitable for electrophoresis are commercially available, and will usually also be provided with a polymer coating as a structural reinforcement. The internal bore of the capillaries will generally range from a few to hundreds of μm. For example, suitable capillaries may range from about 5 to about 300 μm. Preferably, the capillaries utilized range from about 50 to about 75 μm, and are most preferably about 75 μm.

Techniques for operation of capillary electrophoresis separation, and for the operation of chemiluminescence are generally well known. In the practice of the present invention, a sample must first be supplied to the electrophoresis capillary. Well known feed techniques include gravity feed the capillary from a sample source for a timed duration with the electrophoresis powered off, or apply a potential and force the sample into the capillary. The capillary electrophoresis separation is generally operated for about 10 to 20 minutes, usually about 15 minutes. The separated analyte is then contacted with the buffer solution. Electrical current is provided to the buffer current to convert nonluminescening $Ru(bpy)_3^{2+}$ into luminescening $Ru(bpy)_3^{3+}$. Spontaneous luminescence occurs upon contact of the $Ru(bpy)_3^{3+}$ with the analyte. The presence of the analyte is determine by measuring the luminescence.

EXAMPLE

Electrophoresis System

The high voltage for electrophoresis was applied with a Glassman (Whitehouse Station, N.J., model EH30R03.0) 30 kV power supply. Capillaries (75 and 100 μm i.d., 360 μm o.d.) were obtained from Polymicro Technologies (Phoenix, Ariz.). Capillaries were filled by pumping the desired solution into the capillary with a peristaltic pump. Electrical connection was made to both the anodic and cathodic ends of the capillary with Pt electrodes partially submerged in a buffer. The high voltage anode end of the capillary was contained in a Plexiglas box which was equipped with an interlock to prevent accidental operator contact with high voltage. A microammeter was placed in-line between the cathode and the common terminal of the high voltage power supply which allowed monitoring of the electrophoretic current which was passed through the capillary. The entire apparatus was attached to and supported by a 2'×4' optical breadboard which was held at ground potential.

Preparation of the On-Column Nafion Joint

Detection of separated analytes was by chemiluminescence reaction with electrogenerated $Ru(bpy)_3^{3+}$. The electrochemical cell used to generated the $Ru(bpy)_3^{3+}$ was located off-column following decoupling of the electrophoretic field by forming an on-column fracture which was covered with a Nafion tube.

Figure 1:
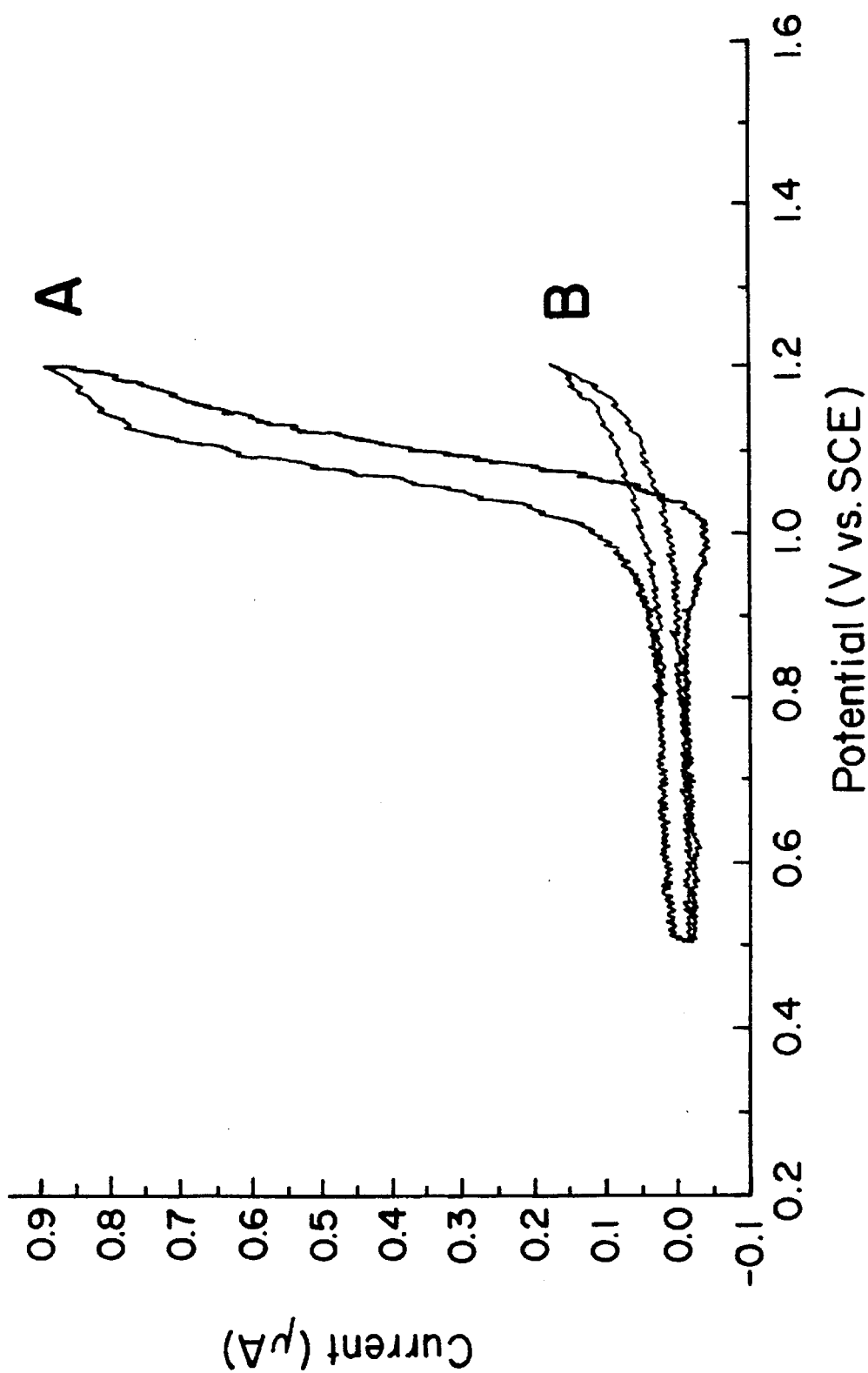
FIG. 1 is a table of current versus potential showing the cyclic voltammetric response of $Ru(bpy)_3^{2+}$ at one of the fibers of the Example experimental apparatus.

Microfiber electrodes were prepared from 35 μm carbon monofilament fibers (available from AVCO, Lowell, Mass.), 0.2 mm copper wire, and glass capillaries by following a proceedure disclosed by O'Shea et al. In J. Chrom., 1993, 644, 208, the article which is herein incorporated by reference. The final electrode length varied from 1 to 4 mm. FIG. 1 is a table of current versus potential showing the cyclic voltammetric response of $Ru(bpy)_3^{2+}$ at one of the fibers.

In FIG. 1, the electrochemical electrolye was 15 mM sodium borate, pH 9.8; sweep rate, 50 mV/s; electrode length is 3 mm. Line A is 1.0 mM $Ru(bpy)_3^{2+}$ present in the electrolyte, and Line B is no $Ru(bpy)_3^{2+}$ present.

Arrangement of Cell

The electrochemical cell was assembled at the end of the detection capillary which extended beyond the Nafion joint and support beaker. The carbon fiber electrode assembly was mounted onto an xyz stage (available from Daedel, Harrison City, Pa.) with a small three-finger lab clamp (available from Fisher, Pittsburg, Pa.). The xyz stage was used to manipulate the carbon fiber into the end of the detection capillary. The carbon fiber served as the working electrode of a 3-electrode assembly. A stainless steel spatula, held by a 3-finger lab clamp served as the auxiliary electrode. The spatula was held at one end by the lab clamp, and the other end acted as a support for a small pool of electrolyte which contacted the carbon fiber and the reference electrode, a saturated calomel electrode ("SCE"). The end of the spatula which supported the electrolyte pool could be raised or lowered by varying the pressure of the adjustment screw of the 3-finger clamp which held the spatula. One leg of the H-cell SCE reference electrode body was held onto the surface of the bread-board, which supported the entire capillary eletrophoresis assembly, by a piece of of Scotch brand (3M) tape. The SCE contacted the electrolyte pool at a point very close to the carbon fiber electrode, and was supported by the spatula serving as the AE. The photomultiplier tube (available from Hamamatsu, N.J., model R928) was mounted over the electrochemical cell so that the photocathode was positioned about 2 cm above the electrolyte solution. High voltage was supplied to the photomultiplier tube by either a Bertan (Hicksville, N.Y., model 215) or a Hewlett-Packard (Palo Alto, Calif., model 6515A) power supply. Potential control of the electrochemical cell was accomplished with a Princeton Applied Research (Princeton, N.J.) model 173 potentiostat and a model 363 universal programmer.

The beaker which supported the capillary joint, the electrochemical cell, and the photomultiplier tube assembly were all contained in a dark-box. The box was constructed from aluminum rods which were supported by the breadboard and was covered with cardboard and black cloth to prevent stray light from reaching the photomultiplier tube. The segment of separation capillary which was located between the Plexiglass box and the dark-box was contained inside a 0.75 inch diameter polyvinyl chloride pipe which was sealed on both ends with a rubber stopper. The PVC pipe prevented accidental operator contact with the capillary which was under high voltage conditions, and helped to prevent light-piping by the capillary into the dark box.

The arrangement of the cell corresponds to the schematic diagram shown in FIG. 2 discussed above.

Data Collection

The output of the photomultiplier tube was fed into a Keithley (Cleveland, Ohio) model 485 picoammeter the output of which was filtered by a 0.15 s time constant before undergoing analog to digital conversion by a Stanford Research Systems (Stanford, Calif.) SR575 lockin amplifier.

Data were ultimately collected by a personal computer interfaced to the SR575 lockin. Cyclic voltammetric data were also collected with the SR575 system. The electrode current during CV experiments was filtered with a 5 ms time constant.

Reagents

Amino acid standards were purchased from Sigma (St. Louis, Mo.) and were used without further purification. Water used for the preparation of electrophoretic buffers was deionized by a mixed-bed ion-exchange cartridge (model #09-034-3, Fisher). $Ru(bpy)_3Cl_2$ was purchased from Aldrich (Milwaukee, Wis.) and converted to the perchlorate salt before use. Sodium hydroxide used in the preparation of electrophoretic buffers was reagent grade (Fisher).

Procedure

Electrophoretic buffers were prepared which contained varying concentrations of $Ru(bpy)_3(ClO_4)_2$. A portion of this $Ru(bpy)_3^{2+}$ was then converted to the active chemiluminescence agent $Ru(bpy)_3^{3+}$, at the off-column electrochemical cell. Eluted amino acids reacted with the $Ru(bpy)_3^{3+}$ to produce chemiluminescence which was observed by the photomultiplier tube. Injected samples were prepared in the $Ru(bpy)_3ClO_4$ buffers.

$Ru(bpy)_3^{2+}$ was not added to the electrophoretic buffer for the end column addition of $Ru(bpy)_3^{2+}$ experiments. Prepared amino acid standards also did not contain $Ru(bpy)_3^{2+}$.

Capillaries used for electrophoretic experiments were pretreated overnight with 0.1 or 1.0M $H_2SO_4$ unless otherwise noted.

Results and Discussion of Experimental Results

Effect of capillary pretreatment with ACID

Lamber and Middleton, Anal. Chem., 1990, 62, 1585, have shown that capillaries pretreated under alkaline conditions and then used for electrophoresis with acidic buffers show a greater rate of electroosmosis than capillaries which were pretreated with acidic solutions.

While not wishing to be bound by theory, the inventors speculate the following. Electroosmotic flow and resolution of analyte peaks in capillary electrophoresis is dependent upon the surface condition of the capillary. Because the surface of the silica contains ionizable silanol groups, the zeta potential and electroosmotic flow rate can vary with capillary pretreatment. Before exposure to liquid ejectrolyte much of the surface of the silica is present as unhydrated silicon dioxide. After exposure to liquid electrolyte, the silica begins to become hydrated to form silanol functionalities. As the silica becomes hydrated, the zeta potential and the electroosmotic flow rate change. Hydration of the silica is known to be a slow process. To aid in the hydration process, some researchers have adopted an alkaline pretreatment procedure which has been shown to be a beneficial procedure in that it increases the rate of electroosmosis.

Experiments were conducted in which capillaries were pretreated with 0.1M or 1M $H_2SO_4$ for at least 12 hours prior to being used in an electrophoresis experiment. The retention characteristics and electrophoretic currents during experiments which followed acid pretreatment were reproducible on a day to day basis. The acid treatments also increased the electroosmotic flow rate. Some trends were noted with these studies. Experiments which were conducted at pH values from 8–8.5 gave better results than those at pH>9. Concentrations of $Ru(bpy)_3^{2+}$ less than 0.5 mM in the electrophoretic buffer also gave better results than experiments with $Ru(bpy)_3^{2+}$ at concentrations greater than 0.3 nM. Prolonged (i.e. >12 hours ) electrophoresis in buffers containing 1 mM $Ru(bpy)_3^{2+}$, even at pH 8.3 resulted in the electrophoretic current rising from relatively low levels (i.e. <15 µA) at the beginning of the experiment to greater than 150 µA. The increased currents caused poor electrophoretic characteristics.

After pretreatment with acidic solutions, the electrophoretic characteristics were very good for triethylamine (TEA) and proline (pro), but were poor for most of the other amino acids exanrined. Triethylarnine and proline at concentrations less than 20 µM usually gave undistorted gaussian-shaped peaks. The other amino acids tested, leucine (leu), valine (val), and phenylalanine (phe) exhibited poorer peak characteristics and were less reproducible than proline and triethylamine.

Figure 3:
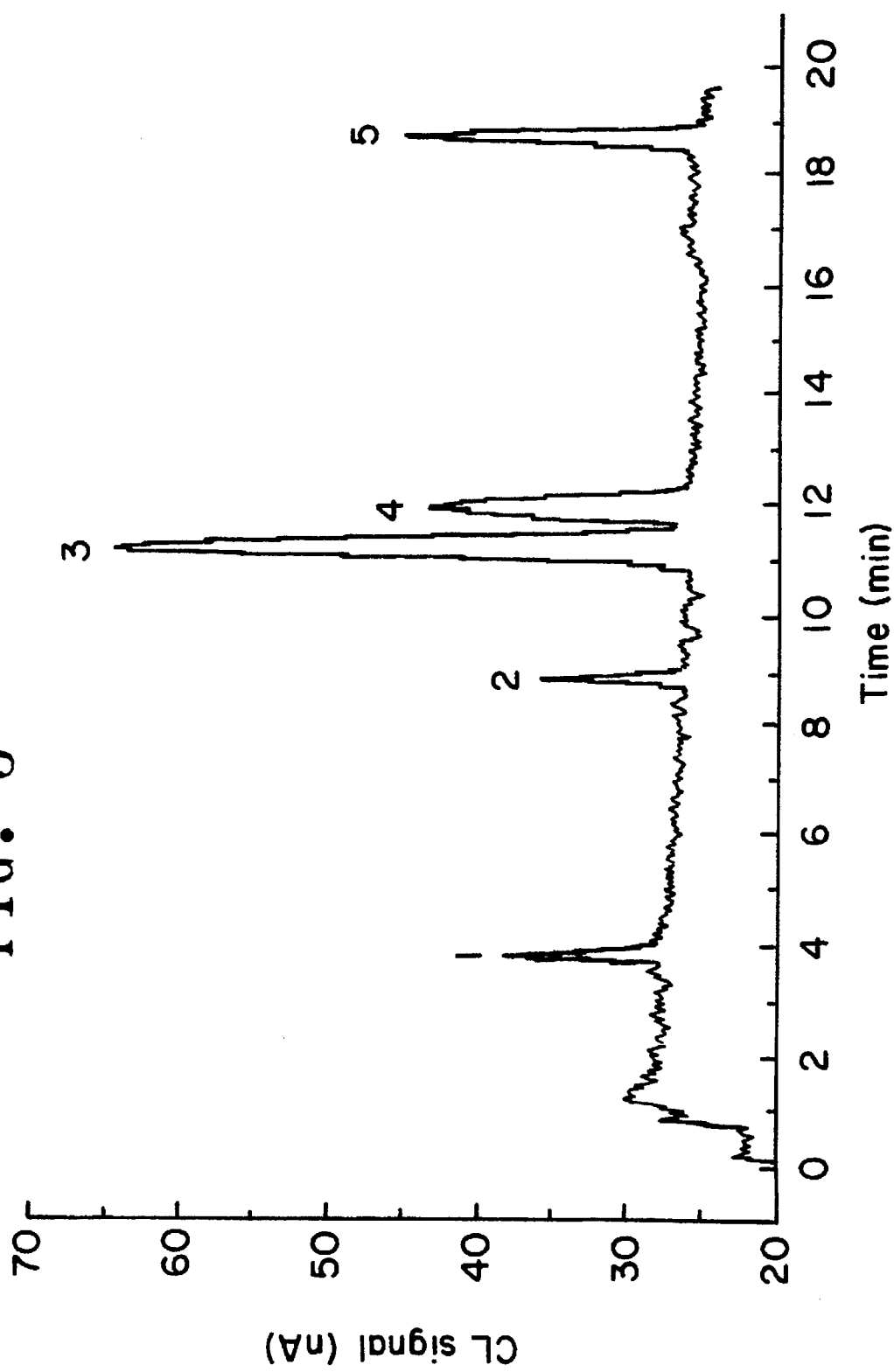
FIG. 3 is an electropherogram of amino acids which was performed on a capillary pretreated overnight with $0.1M$ $H_2SO_4$ as described in the Example.

FIG. 3 shows an electropherogram of triethylamine, proline, leucine, valine, and phenylalanine performed on a capillary which was treated overnight in 0.1M $H_2SO_4$. The capillary used was 75 µm i.d., 50 cm long, with a 5 cm detection capillary. The electrophoretic buffer was 15 mM borate, pH 8.5, with 0.5 mM $Ru(bpy)_3^{3+}$ added for detection which was by chemiluminescence of the amino acids with in-situ generated $Ru(bpy)_3^{3+}$. The generator electrode was a 35 µm diameter carbon fiber held at 1.15 V vrs. The reference electrode. The photomultiplier tube was biased at 900 V. Separation conducted at 25 kV, injection was for 5 s at 25 kV. Peak identification: 120 fmol triethylamine (1); 40 fmol proline (2); 1 pmol leucine (3); 1 pmol valine (4), and 1 pmol phenylalanine (5). Note the broad responses for leucine and valine, and the small baseline rise before phenylalanine was eluted. This represents some of the best data collected. At times leucine, valine, and phenylalanine were observed to be very broad peaks which were hardly observable even at high concentration levels (i.e. mM). The cause is unknown, although interaction with $Ru(bpy)_3^{3+}$ adsorbed onto the negatively-charged silica surface is suspected.

Freshly-prepared capillaries produced gaussian-shaped peaks for triethylamine and proline after being used for several hours in pH 8–8.5 buffers which contained 15 mM borate, and 0.2 mM $Ru(bpy)_3^{2+}$. However, leucine, valine, and phenylalanine were often very broadened as described above. Characteristics varied from capillary to capillary. No definitive protocol was developed for improving the electrophoretic characteristics of leucine, valine, and phenylalanine, but peak shapes did improve somewhat with use of the capillary in electrophoresis experiments. It is possible that the Nafion field decoupler is responsible for some of the unusual electrophoretic characteristics, but similar electrophoretic results were obtained in the absence of a field decoupler.

Figure 4A:
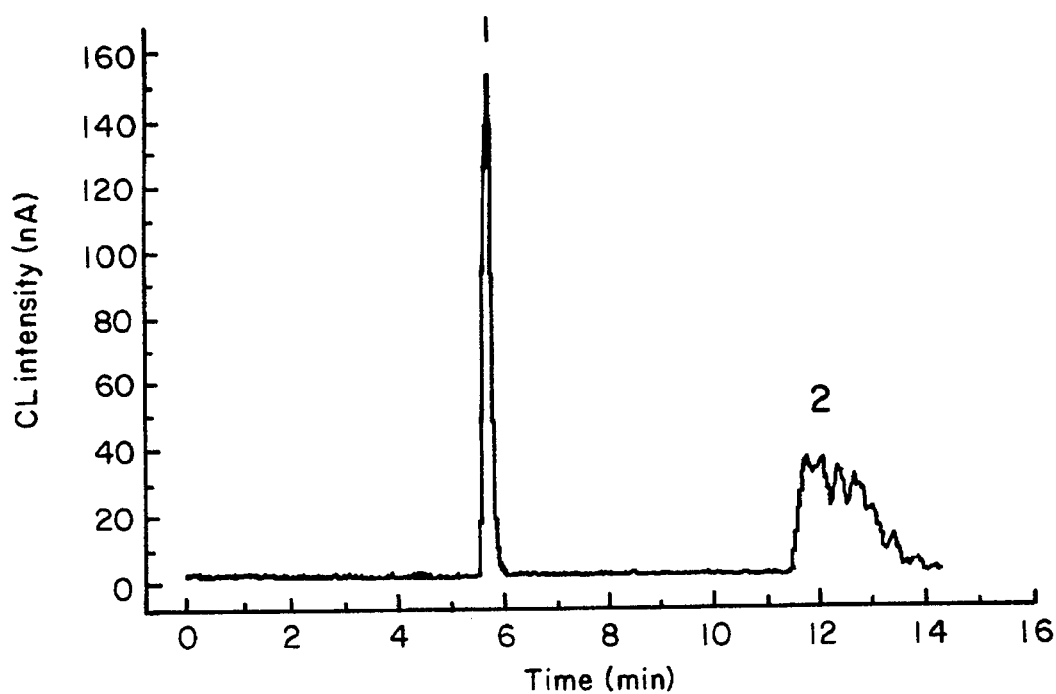
FIGS. 4A and 4B are graphs of measured intensity versus time for proline both before (FIG. 4a) and following (FIG. 4B) a capillary wash with $0.1M$ $H_2SO_4$ as described in the Example, showing improvement in the peak resolution after the wash.

Proline at concentrations less than 20 µM provided gaussian peak shapes upon elution. Concentrations greater than 20 µM would frequently yield distorted peaks upon elution. FIGS. 4A (before wash) and 4B (after wash) show dramatic evidence of the improvement of the peak shape for an injection of 200 µM proline following a 15 minute wash of the capillary with 0.1M $H_2SO_4$. The capillary used was 75 µm i.d., 62 cm long, with a 5 cm detection capillary. The electrophoretic buffer was 15 mM borate, pH 8.5, with 0.2 mM $Ru(bpy)_3^{2+}$ added for detection which was by chemiluminescence of the amino acids with in-situ generated $Ru(bpy)_3^{3+}$. The generator electrode was a 35 µm diameter carbon fiber held at 1.15 V vrs. The reference electrode. The photomultiplier tube was biased at 900 V. Separation conducted at 25 kV, injection was for 5 s at 25 kV. The electrophoretic current was 6 µA.

Figure 4B:
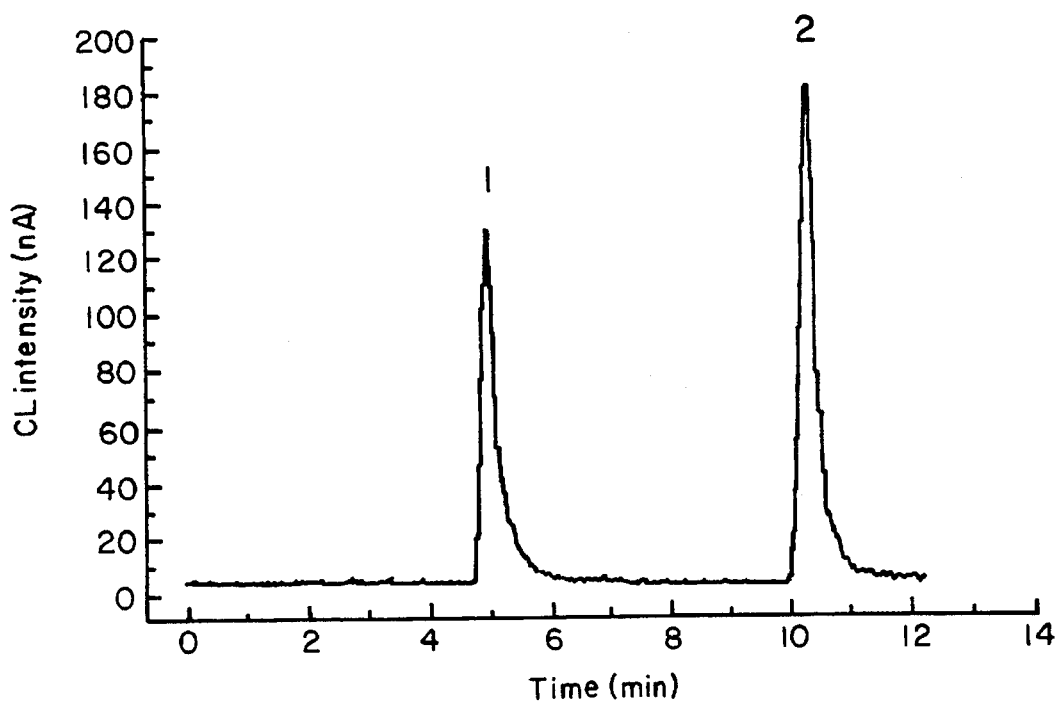

In FIG. 4A, before the acid wash, the peak corresponding to proline was very broad and distorted. In FIG. 4B, after the acid wash, the peak was very sharp, although it showed a bit of tailing. Both the triethylamine and proline peaks show tailing after the acid wash. The peaks also eluted at an earlier time, indicating increased electroosmotic flow through the capillary.

Notice that this result is in contrast to the above discussed results presented by Lambert and Middleton which showed that the electroosmosis was slower through capillaries which had been treated with acidic solutions. This is evidence for the strong adsorption of the large Ru(bpy)$_3^{2+}$ cation onto the surface of the silica capillary. Washing with the 0.1M H$_2$SO$_4$ probably displaces the Ru(bpy)$_3^{2+}$ cation from the surface. The effect of the acid wash on the shape of proline was rather short lived. Some peak distortion was noted in proline in the second injection following the acid wash although the distortion was not nearly as severe as in FIG. 4A.

The capillary used for these studies was stored each night in 0.1M H$_2$SO$_4$ before being used the following day. The capillary provided good day to day electrophoretic characteristics over the course of the study which was approximately 1 month.

Dependence of electroosmotic flow rate upon the concentration of Ru(hpy)$_3^{2+}$ and Na+ the electrophoretic buffer.

Figure 5:
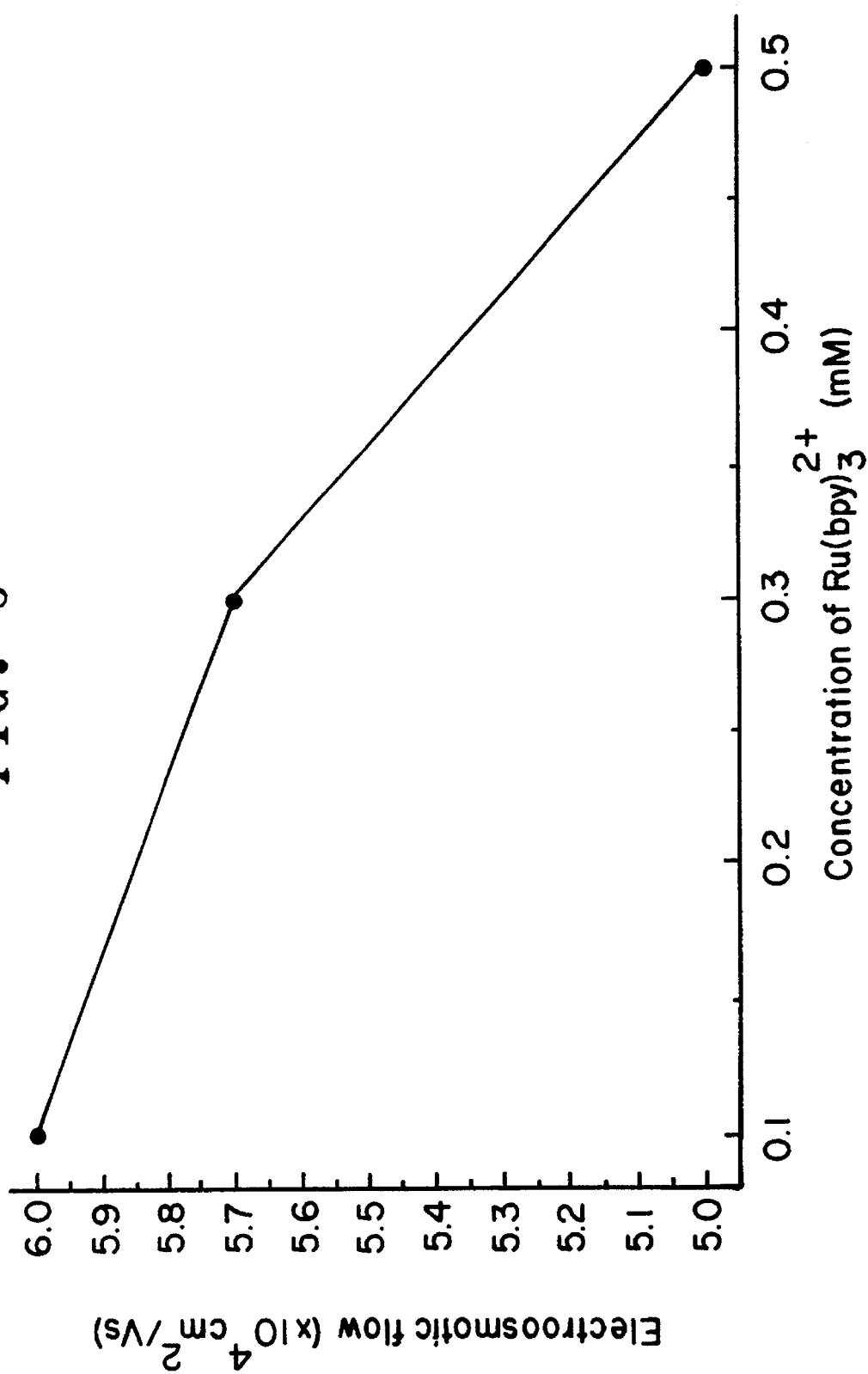
FIG. 5 is a graph of electroosmotic flow versus concentration of $Ru(bpy)_3^{2+}$ as decribed in the Example, showing a reduction in the rate of electroosmosis as the concentration of $Ru(bpy)_3^{2+}$ in the electrophoretic buffer is increased.

FIG. 5 shows how the elution time of water, used as a neutral marker, changed on going from 0.1 mM to 0.5 mM Ru(bpy)$_3^{2+}$ at pH 8.5. Capillary is 75 µm i.d., 360 o.d., 50 cm in length, with a 5 cm detection capillary segment. Buffer is 15 mM borate, adjusted to pH 8.5 with NaOH, with other parameters same as those for FIG. 4 above.

Detection was again by Ru(bpy)$_3^{2+}$ chemiluminescence. To obtain the elution times for water, a sample of buffer without added Ru(bpy)$_3^{2+}$ was injected into the system. A negative peak resulted which was concluded to be water. Amino acid retention times were increased as a result of the decrease in the electroosmotic flow rate. The final equation derived provided an excellent fit to their experimental data, and is shown below.

$$\mu_{eo} = Qo/\eta(1+K_{wall}[M^+])(d_o+1/K'([M+]^{0.5})) \quad 1$$

where $\mu_{eo}$ is electroosmotic flow, $Q_0$ is the total number of ionized silanol groups at the capillary surface, $\eta$ is viscosity, $K_{wall}$ is the equilibrium constant describing the interaction between adsorbed cations and ionized silanol groups, [M+] is the buffer cation, $d_0$ is the electrical double layer thickness, and K' is a constant. This equation predicts that $\mu_{eo}$ should decrease as [M+] increases.

This equation was derived and applied to electrophoresis experiments in which only one type of cation, other than H$^+$, was present in the electrophoretic buffer. The detection scheme investigated in the present study necessitated the presence of at least two cations in the electrophoretic buffer: Ru(bpy)$_3^{2+}$ and Na$^+$. While an increase in Ru(bpy)$_3^{2+}$ caused the expected decrease in $\mu_{eo}$, an increase in the concentration of Na$^+$ caused an increase in $\mu_{eo}$. The borate buffer concentration was increased from 15 to 45 mM, while the pH was held constant. This effectively results in the concentration of Na$^+$ being increased by a factor of 3. At 15 mM borate, the $\mu_{eo}$ was found to be 5.9×10$^{-4}$ cm2/V s, while at 45 mM borate the $\mu_{eo}$ was 6.4×10$^{-4}$ cm2/V s as measured with the neutral marker, water. This increase in $\mu_{eo}$ with increased Na$^+$ concentration seems somewhat anomalous. However, there is a likely explanation for the apparent anomaly. When two cations are present in the buffer, each will adsorb to the capillary wall with different affinities. This leads to the establishment of a $K_{wall}$ for each cation which is present. Both $K_{wall}$ and $d_0$ will likely be affected by the change in the relative concentrations of both cations. However, if EQN. 1 can be used to describe the binary cation situation, the following approach justifies the observed result. As the buffer concentration is increased, [Na+] increases which, taken alone, predicts a decrease in based on equation 1. Other parameters which can change significantly at constant pH within the binary cation system are Kwall and $d_0$. The expression describing Kwall is shown below.

$$K_{wall}[SiO^-M^+]/[M+] [SiO^-] \quad 2$$

Consider an average $K_{wall}$ in the presence of two cations, $K_{avg} = xK_{Ru} + yK_{Na}$, where $K_{Ru}$ is the equilibrium constant between the silica surface and Ru(bpy)$_3^{2+}$, $K_{Na}$ is the equilibrium constant between the silica and the sodium ion, and x and y are relative contributions to $K_{avg}$ by each of the equilibria. In the absence of either ion, the $K_{avg}$ becomes the Kwall for the ion which is present. It is reasonable that x and y will be directly proportional to the relative concentration of that particular cation in the electrophoretic buffer. This means that if the sodium ion contributes 80% of the total cation concentration in the buffer, y will be larger than if sodium contributes only 40% of the total cation concentration. The argument then leads to the conclusion that $K_{Na}$ is smaller than $K_{Ru}$ since $K_{wall}$ must have decreased as the concentration of the sodium ion increased. This is additional evidence in support of strong Ru(bpy)$_3^{2+}$ adsorption onto the wall of the silica capillary.

It is also very likely that $d_0$ changes with the relative change in cation concentrations. $d_0$ generally decreased as cation size increased. The electroosmotic flow increases as $d_0$ increases. An extension to $d_0$ of the argument made above concerning $K_{wall}$ indicates that $d_0$ is expected to increase as the relative concentration of sodium ion increases which would lead to an increase in $\mu_{eo}$. It is likely that both of these parameters are changing and give rise to the observed increase in $\mu_{eo}$.

Limit of detection and lineality characteristics.

Figure 6:
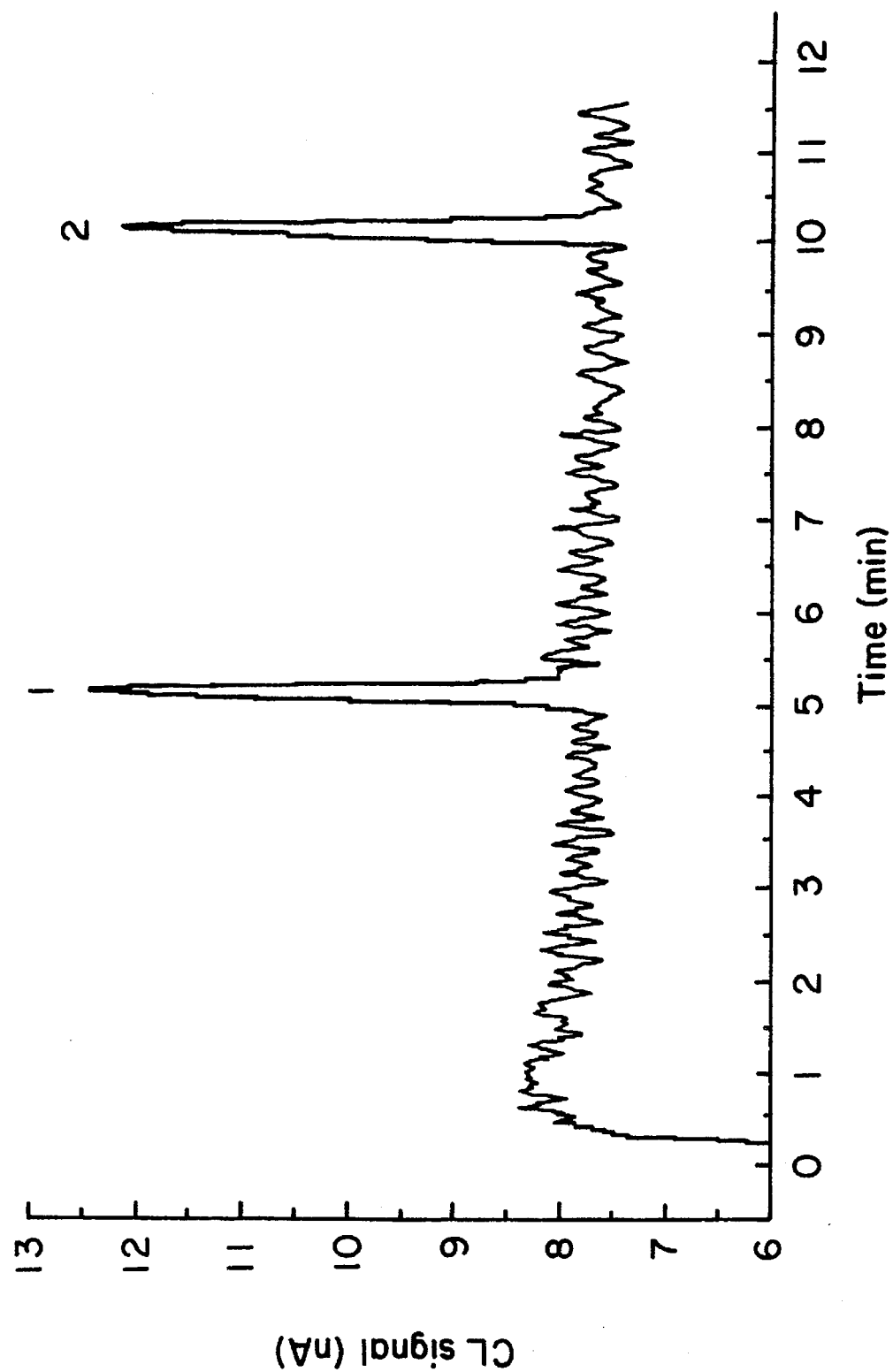
FIG. 6 is an electropherogram of triethylamine and proline which was used to estimate limits of detection of the experimental apparatus.

Most of the electrophoretic data collected was at pH 8–9. These pH values are below the pH values of maximum Chemilumenescence intensity for the amino acids which is near pH 10 (34). However, the CE was much more reproducible within the pH 8–9 range than at pH 10 probably because of adsorption of Ru(bpy)$_3^{2+}$ onto the silica capillary as described earlier. The limit of detection for triethylamine and proline were estimated from a 5 s electrokinetic injection (at 25 kV) of a 2 µM solution of each into a 75 pm capillary. At pH 8.5 and the concentration of Ru(bpy)$_3^{2+}$ at 0.2 mM, the limit of detection for triethylamine at a signal to noise ratio (SNR) of 3 was estimated to be approximately 200 nM (8 fmol), and for proline was 200 nM (4 finol). The absolute mass limit of detection is lower for proline since less proline is injected by the electrokinetic method. FIG. 6 shows the electropherogram of triethylamine and proline from which the limits of detection were estimated. The capillary used was 75 µm i.d., 62 cm long with a 5 cm detection capillary. Buffer was 15 mM borate, pH 8.5, with 0.2 mM Ru(bpy)$_3^{2+}$ added. Electrode used for in situ generation of Ru(bpy)$_3^{3+}$ was 35 µm diameter carbon fiber which was 3 mm long held at 1.15 V vrs. the reference. Peaks represent approximately 80 fmol TEA (1) and 40 fmol pro (2). Separation conducted at 25 kV with injection for 5 s at 25 kV.

In FIG. 6, the noise in the baseline which is limiting the sensitivity of the measurement is very periodic. It was determined in a separate experiment that the standard deviations of the background are essentially the same (approximately 0.2 nA) with and without the electrochemical cell activated.

From this data, it was concluded that the major contributor to the noise level with the capillary system is located within the electronics of the light collection system and not within the electrochemical system used to generate the Ru(bpy)$_3^{3+}$. Although the exact source of the noise is not known, random thermal emission from the photocathode of the photomultiplier tube is a likely source. The photomultiplier used for this Example is not designed for applications requiring the detection of ultralow light levels. According to literature supplied by the manufacturer, the observed standard deviations in the noise are typical of the darknoise observed with this photomultiplier tube at room temperature. Cooling of the photomultiplier tube might provide improved the limits of detection.

The linearity of proline cannot be estimated easily with the electrophoretic method because of peak distortion which appears above 20 µM in concentration, as discussed earlier. However, there is roughly a 10× increase in peak signal on going from 2 to 20 µM injected proline. The chromatographic efficiency of the system is quite good as seen from FIG. 6. The number of theoretical chromatographic plates for the proline peak in FIG. 6 is about 20000.

A capillary flow-injection technique was used to estimate the limit of detection and linearity characteristics of leucine and serine. A 75 µm i.d. capillary which was 60 cm in length was used for the flow injection experiments. Samples were gravity injected by raising the injection end of the capillary about 20 cm above the detection end of the capillary. The buffer used for the studies was 15 mM borate at pH 9.8 with 1 mM Ru(bpy)$_3^{2+}$ added for in situ detection The PMT was biased at 900 V. This experiment yielded very gaussian albeit very broad responses for the amino acids. The limits of detection calculated at a SNR of 3 for leucine from these experiments was 330 nM (27 fmol) and for serine was 20 µM (1.6 pmol). A log-log plot of concentration vrs. signal for leucine showed a linear response from 1 µM to 100 µM leucine injected (N=6, y=1.22 (±0.04)x–0.18 (±0.05), r$^2$=0.996). These concentration limits of detection are not as low as those realized earlier with the larger flow cell with the glassy carbon disks (27). In that application, leucine was determined to have a limit of detection of 45 riM and serine 1.1 NM. As described earlier, the likely reason for the poorer detection limits with the capillary-based system is related to the very low light levels which must now be detected. While these limits of detection in terms of amino acid concentrations are poorer than those seen with the larger electrochemical cell, they are still very competitive with other methods used to detect native amino acids in chemiluminesence.

In situ generated chemiluminescence detection of amino acids with end column addition of Rn(bpy)$_3^{2+}$.

Addition of Ru(bpy)$_3^{2+}$ to the electrophoretic buffer seemed the most logical and experimentally convenient way to provide a constant source of Ru(bpy)$_3^{2+}$ for in situ conversion to Ru(bpy)$_3^{3+}$ and subsequent chemiluminescence reaction and detection of amino acids following CE. However, with the problems described earlier, which are believed to result from strong adsorption of Ru(bpy)$_3^{2+}$ onto the capillary surface, this approach does not seem very practical for the routine separation and analysis of amino acids. The in situ generation of Ru(bpy)$_3^{3+}$ at the carbon fiber works very well for the chemiluminescence detection of amino acids at capillary dimensions, but the Ru(bpy)$_3^{2+}$ causes problems with the electrophoresis.

Figure 7:
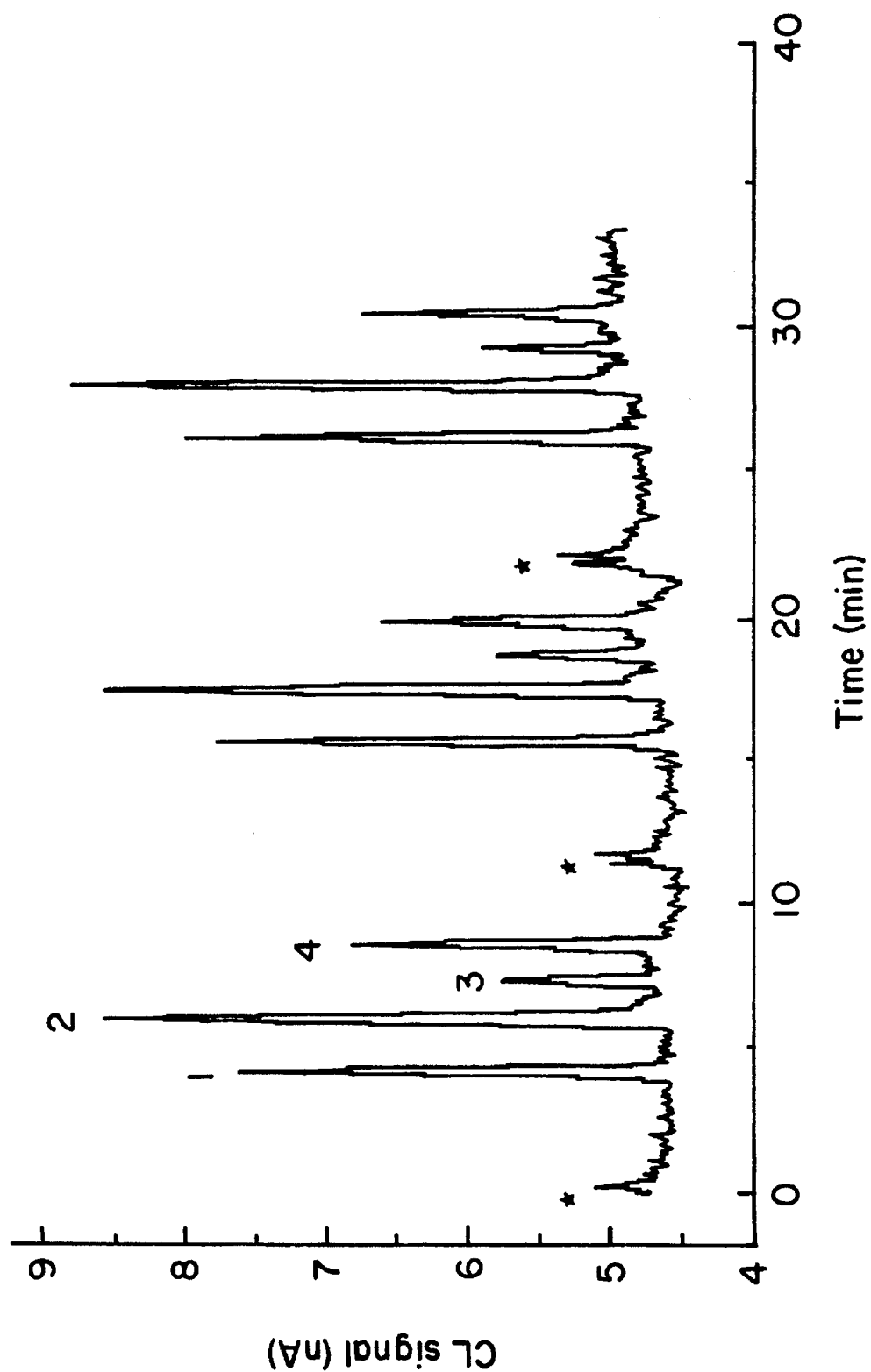
FIG. 7 is an electropherogram of amino acids with end column addition of 1 mM $Ru(bpy)_3^{2+}$ as described in the Example.

End column addition of Ru(bpy)$_3^{2+}$ was examined as a way to avoid addition of Ru(bpy)$_3^{2+}$ to the electrophoretic buffer, while still allowing the chemiluminescence detection of amino acids by reaction with in situ generated Ru(bpy)$_3^{3+}$. Bulk Ru(bpy)$_3^{3+}$ will be difficult to mix in an end column fashion with eluting amino acids due to its instability at alkaline pH values which are required for efficient separation and detection of the amino acids. A drop (~100 µL) of 15 mM boric acid solution at about pH 5 which contained 1 mM Ru(bpy)$_3^{2+}$ was placed at the end of the detection capillary and served as the electrochemical electrolyte for the detection cell. This configuration is identical to that used earlier, but Ru(bpy)$_3^{2+}$ was not added to the electrophoretic buffer. Triethylamine, proline, valine, and serine were injected, separated, and detected by their chemiluminescence reaction with in situ generated Ru(bpy)$_3^{3+}$. FIG. 7 shows three injections of this mixture.

FIG. 7 is an electropherogram of amino acids with end column addition of 1 mM Ru(bpy)$_3^{2+}$. Separation conducted at 20 kV with injection of analytes for 8 s at 20 kV. Other conditions are the same as noted in FIG. 6, except there is no Ru(bpy)$_3^{2+}$ in the electrophoretic buffer, and the pH of the buffer is 9.5. Peak identification: (1)100 fmol TEA, (2) 70 fmol pro, (3)1.6 pmol val, (4) 50 pmol ser. Injection points denoted by ("*").

The reproducibility between the inlections is very good. The Ru(bpy)$_3^{3+}$ which reacts with the eluting amino acids is apparently mixed with the amino acids by convection and difusion. This technique does not have the benefit of the mass transport of both the amino acid and Ru(bpy)$_3^{2+}$ to the electrode surface by the electroosmotic flow which enhances the chemiluminescence reaction, but does seem to provide for efficient mixing and chemiluminescence reaction. The greatest advantage to this scheme is that the electrophoresis will not be inhibited by the presence of Ru(bpy)$_3^{2+}$ and will likely find application to the separation and detection of all of the amino acids and important derivatives such as the PTH amino acids used in protein sequence analysis.

These preliminary experiments suggest that end column addition of Ru(bpy)$_3^{2+}$ will be at least one solution to elimination of Ru(bpy)$_3^{2+}$ from the electrophoretic buffer while still allowing the sensitive detection of the amino acids by in situ generated chemiluminescence following chemiluminescence separation. This approach is also very easily implemented with the experimental system described earlier and will greatly enhance the versatility of the chemiluminescence separation I chemiluminescence detection scheme by allowing application to all of the native amino acids.

The present invention is believed to have applicability for detecting amines, amino acids, peptides, proteins, and compounds having any of the foregoing as functional groups. Specifically, the present invention is also believed to to have applicability for detecting all 22 of the naturally occuring amino acids.

While the illustrative embodiments of the invention have been described with particularity, it will be understood that various other modifications will be apparent to and can be readily made by those skilled in the art without departing from the spirit and scope of the invention. Accordingly, it is not intended that the scope of the claims appended hereto be limited to the examples and descriptions set forth herein but rather that the claims be construed as encompassing all the features of patentable novelty which reside in the present invention, including all features which would be treated as equivalents thereof by those skilled the art to which this invention pertains.

I claim:

1. A method for detecting an analyte in a sample, where the analyte is selected from amines, amino acids, peptides, proteins, and compounds having any of the foregoing as functional groups, the method comprising:

(a) introducing the sample into an electrophoresis capillary to separate the analyte from the sample to form a separated sample;

(b) directing the separated sample from the capillary into a contacting zone for immediate contact with a solution, wherein the zone is electrically decoupled from and located adjacent to the capillary, wherein the solution comprises $Ru(bpy)_3^{2+}$ which is being electrically converted to $Ru(bpy)_3^{3+}$, and wherein luminescence is produced once the separated sample contacts any $Ru(bpy)_3^{3+}$ in the solution;

(c) photometrically measuring the quantity of analyte present as a function of the luminescence.

2. The method of claim 1 wherein the analyte is an amine or an amino acid.

3. The method of claim 1 wherein the capillary tube is first pretreated by contacting the tube with an acid.

4. The method of claim 1 wherein the pH of the solution is in the range of about 8.0 to about 8.5.

5. The method of claim 1 wherein the analyte is an amine or an amino acid, the capillary tube is first pretreated by contacting the tube with an acid, and the pH of the solution is in the range of about 8.0 to about 8.5.

6. An apparatus for detecting an analyte in a sample, where the analyte is selected from amines, amino acids, peptides, proteins, and compounds having any of the foregoing as functional groups, the apparatus comprising:

(a) an electrophoresis separator capillary for separating the analyte from the sample, having an exit end;

(b) a reaction zone located adjacent the exit end for receiving the analyte from the separator tube;

(c) an electronic decoupler positioned to electronically decouple the electrophoresis separator capillary from the reaction zone;

(d) a reservoir of $Ru(bpy)_3^{2+}$ located in the reaction zone;

(e) an electrode assembly in contact with the reservoir to convert $Ru(bpy)_3^{2+}$ into $Ru(bpy)_3^{3+}$; and (f) a photometric measuring device which photmetricaly measures the quantity of analyte.

7. The apparatus of claim 6 wherein the capillary comprises an acid pretreated capillary.

8. The apparatus of claim 6 wherein the capillary comprises a sulfuric acid pretreated capillary.

* * * * *